United States Patent [19]
Mitschke et al.

[11] Patent Number: 6,034,260
[45] Date of Patent: Mar. 7, 2000

[54] DIALKYLPHOSPHORIC ACIDS BY THE METHANOL METHOD

[75] Inventors: Karl-Heinz Mitschke, Odenthal; Christoph Holzner, Köln, both of Germany

[73] Assignee: Bayer AG, Germany

[21] Appl. No.: 09/267,465

[22] Filed: Mar. 11, 1999

[30] Foreign Application Priority Data

Mar. 18, 1998 [DE] Germany ............................ 198 11 483

[51] Int. Cl.$^7$ ...................................................... C07F 9/09
[52] U.S. Cl. .................................................. 558/92; 562/8
[58] Field of Search ............................ 558/92, 99; 562/8

[56] References Cited

U.S. PATENT DOCUMENTS

| | | |
|---|---|---|
| 2,960,527 | 11/1960 | Grunze . |
| 3,155,706 | 11/1964 | Camacho . |
| 3,657,398 | 4/1972 | Ismail . |
| 3,737,487 | 6/1973 | Nichols . |
| 4,034,023 | 7/1977 | Hardy . |
| 4,288,392 | 9/1981 | Horn et al. ............................ 260/983 |
| 4,296,047 | 10/1981 | Schmidt . |

FOREIGN PATENT DOCUMENTS

| | | |
|---|---|---|
| 33 999 | 8/1981 | European Pat. Off. . |
| 1 024 520 | 2/1958 | Germany . |

OTHER PUBLICATIONS

Von J. Perka and S. Ropuszynski, *Tenside Detergents*, vol. 15, 6, Untersuchungen uber die Phosphorylierung des 2–Athylhexyl alkohols und die Abtrennung der Di–(2–Athylhexyl)–Phosphorsaure als Kupfersalz, pp. 295–298 (1978).

Methoden der Org. Chemie (Houben–Weyl), vol. 12/2, Georg Thieme Verlag Stuttgart, pp. 239, 252–257 (1964).

Methoden der Org. Chemie (Houben–Wyel), vol. E2, Org. Phosphorverb. II, pp. 498–499, Georg Thieme—Verlag Stuttgart (1982).

Harold D. Orloff, Calvin J. Worrel, Francis X. Markley, *The Journal of the American Chem. Society*, vol. 80, The Synthesis of Alkyl Aryl Phosphates from Aryl Phosphorchloridates, II. The Sovolysis Route, pp. 734–739 (1958).

CA:116:255813 abs of Br9000781, Oct. 1991.

CA:113:8389 abs of Pr Nauk Akad Ekon im Oskara Langego Wroclawiu by Pinkowska 476 pp. 123–133, 1989.

CA:78:83941 abs of Sb Nauch Tr Kim Sverdlovsk Inst Nat Khoz pp. 89–90, 1972.

*Primary Examiner*—Gary Geist
*Assistant Examiner*—Jean F Vollano
*Attorney, Agent, or Firm*—Connolly, Bove Lodge & Hutz LLP

[57] ABSTRACT

The present invention relates to a process for the preparation of symmetrically substituted phosphoric acid diesters of long-chain linear or branched alcohols of chain length $C_4$ to $C_{22}$.

19 Claims, No Drawings

DIALKYLPHOSPHORIC ACIDS BY THE METHANOL METHOD

The present invention relates to a process for the preparation of symmetrically substituted phosphoric acid diesters of long-chain linear or branched alcohols of chain length $C_4$ to $C_{22}$.

Phosphoric acid diesters of long-chain alcohols have applications in textile treatment as wetting and anti-static agents and in hydrometallurgy as extracting agents.

The simplest method of preparing them hitherto, which comprises reacting from 1 to 3 moles of a $C_4$ to $C_{22}$ alcohol with 1 mole phosphorus oxychloride, has afforded a crude product which—depending on the molar ratio of the two feedstocks used—contains in addition to the desired diester a sizeable proportion of phosphoric acid monoester or triester.

J. Perka and S. Ropuszynski in Tenside Detergents, Vol. 15, issue 6, (1978), pages 295 to 298, describe the reaction of 2-ethylhexanol with phosphorus oxychloride. At a feedstock molar ratio of alcohol/$POCl_3$ of 1.435/1.1, the crude product contains 20% monoester, 72.4% diester and 7.6% triester (see J. Perka and S. Ropuszynski, page 296, Table 1, No. 2). Increasing the feedstock molar ratio to 2/1 increases the triester content at the expense of the monoester, while the diester content remains virtually unchanged at 70.3% (ibid., Table 1, No. 3).

Even in the presence of a specific catalyst (1% boron trifluoride etherate as an additive) the diester content of the crude product cannot be increased above 76.0% (ibid., Table 1, No. 10).

Because of the need for substantially higher degrees of purity for the applications mentioned at the outset, Perka and Ropuszynski propose elaborate purification processes:

The "selective solubility method" involves dissolving the crude product in benzene and washing it twice with from 1 to 0.5 M sodium hydroxide solution, twice with 6 M hydrochloric acid and three times with distilled water. This purification process gives very good results if the chief impurity present is monoester, the sodium salt of which is sufficiently water-soluble. If, on the other hand, the chief impurity present is triester, which is incapable of salt formation, the purifying effect is inadequate (ibid., page 296, Table 2, No. 5). In this case the diester must be separated as the copper salt (ibid., page 297), a process which is uneconomic due to the high consumption of chemicals (sodium hydroxide solution, hydrochloric acid, benzene, acetone, copper sulphate).

Because of the difficulty of obtaining the pure diester starting from alcohol and phosphorus oxychloride, it has also been proposed to prepare the triester first, using feedstock molar ratios of $\geq 3$, followed by saponification with sodium hydroxide solution (see Methoden der Organischen Chemie (Houben-Weyl), Vol. 12/2, pages 252 to 254, Georg Thieme Verlag Stuttgart, 1964). However, this process is very laborious and cost-intensive. HCl gas and excess alcohol must first be removed from the triester. The triester is then saponified, consuming 1 mole sodium hydroxide solution per mole triester and necessitating once more the separation of alcohol, plus the use of an equivalent quantity of mineral acid in order to convert the resulting sodium salt of phosphoric acid diester into the free dialkylphosphoric acid. At the end of this process there remains an organically loaded aqueous sodium chloride or sulphate solution which constitutes unusable waste.

The literature also proposes using the hydrogen chloride resulting from the reaction between phosphorus oxychloride and alcohol to cleave the triester (see Methoden der Organischen Chemie (Houben-Weyl), Vol. 12/2, page 239, Georg Thieme Verlag Stuttgart, 1964). The reaction sequence:

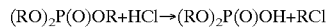

gives rise, in addition to dialkylphosphoric acid, to an equimolar quantity of alkyl chloride. If long-chain dialkylphosphoric acids are prepared, long-chain alkyl chlorides also arise which must generally be disposed of at great cost by incineration.

Phosphoric acid monoaryl ester dichlorides react with methanol (see Harold D. Orloff, Calvin J. Worrel, Francis X. Markley: The Journal of the American Chemical Society, Vol. 80, pages 734 to 739, (1958)) or $C_1$ to $C_3$ alcohols (see German Patent Specification No. 906 808, issued on Mar. 18, 1954) or $C_1$ to $C_4$ alcohols (see German Auslegeschrift No. 1 024 520, issued on Feb. 20, 1958) to form asymmetrically substituted phosphoric acid arylalkyl esters, wherein the reaction sequence:

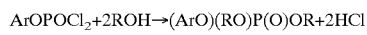

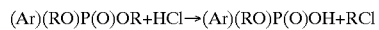

gives as a by-product a valuable short-chain alkyl chloride. It is a disadvantage of the latter formula that only mixed arylalkyl phosphates are obtained. The aryldialkyl phosphate which arises as an intermediate product is cleaved by the hydrogen chloride at one of the two alkyl groups, but not at the aryl group which is known to be cleavable readily by alkaline hydrolysis but only with great difficulty by acid hydrolysis (see Methoden der Organischen Chemie (Houben-Weyl), Vol. 12/2, pages 254 and 255, Georg Thieme Verlag Stuttgart, 1964). The selectivity of the cleavage of the mixed triester by hydrogen chloride is favoured not only by the difference in reactivity between aryl and alkyl groups but also by the laws of probability: twice as many alkyl groups as aryl groups are available for cleavage.

The syntheses known hitherto for symmetrical long-chain phosphoric acid diesters generally proceed via the phosphorous acid diesters as intermediate products. Phosphorous acid diester preparation from the relevant alcohol and phosphorus trichloride is possible at higher yields and purity than phosphoric acid diester preparation from alcohol and phosphorus oxychloride. However, oxidation to the corresponding phosphoric acid derivative is necessary subsequently, and this requires the use of highly reactive, toxic oxidants. EP 0 033 999, for instance, describes the oxidation of phosphorous acid diesters with chlorine. Further oxidants such as bromine, nitrogen oxides, chlorine dioxide and oxygen-ozone mixtures are mentioned in Methoden der Organischen Chemie (Houben-Weyl), Vol. E2, Organische Phosphorverbindungen II, pages 498 to 499, Georg Thieme Verlag Stuttgart, 1982). The formation of by-products such as aldehydes, carboxylic acids or chlorohydrocarbons, which may arise as a result of undesirable oxidation of the alkyl groups, is a problem. On the other hand, phosphorus trichloride is oxidised successfully to phosphorus oxychloride with atmospheric oxygen in a smooth reaction without the formation of organic by-products. Because phosphorus is converted particularly cleanly and economically into the desired oxidation state +5 by the latter reaction, phosphorus oxychloride is the most economically attractive raw material for preparing phosphoric acid esters.

The object of the present invention is to provide, starting from phosphorus oxychloride, a process for the preparation of symmetrical long-chain dialkylphosphoric acids, which delivers the desired products by the simplest possible method, at high purity and without the occurrence of significant quantities of waste substances.

The present invention provides, and hence the object is achieved by, a process for the preparation of symmetrical phosphoric acid diesters from long-chain linear or branched alcohols of chain length $C_4$ to $C_{22}$ and phosphorus oxychloride, characterised in that a) from 1 to 4 moles, preferably 1.3 to 2.5 moles, phosphorus oxychloride are reacted with 1 mole methanol, b) the resulting hydrogen chloride is removed from the reaction mixture by the application of a vacuum or by passing an inert gas through the reaction mixture, c) any excess phosphorus oxychloride still present is distilled off, d) the remaining reaction mixture is reacted with from 2 to 6 moles of a linear or branched alcohol of chain length $C_4$ to $C_{18}$, e) the chloromethane arising in a post-reaction is evaporated off or is removed from the reaction mixture by passing through the latter an inert gas, hydrogen chloride or a mixture of both gases, f) water-soluble, readily volatile substances are removed from the reaction mixture by
  i) passing inert gas through the reaction mixture, or
  ii) washing with water or
  iii) carrying out a steam distillation or a combination of the latter three process steps, followed by initial distillation under vacuum.

The reaction between methanol and phosphorus oxychloride (step a)) is preferably carried out at a temperature of from −5 to +30° C., particularly preferably +5 to +10° C. It has proved to be particularly advantageous to have the phosphorus oxychloride at the desired temperature and to add the methanol to it with cooling. This ensures from the start an excess of phosphorus oxychloride in the reaction mixture. A post-reaction of from 0.5 to 2 hours' duration at the same temperature suffices to react the feedstocks in accordance with the reaction equation $$CH_3OH+POCl_3 \rightarrow CH_3OPOCl_2+HCl.$$

The resulting hydrogen chloride gas (step b)) is then pumped off by lowering the pressure to 20 to 100 mbar, preferably 50 mbar, at a bottom temperature of from 10 to 30° C., preferably 20 to 25° C., or is removed from the reaction mixture by introducing a dry inert gas such as nitrogen, air or carbon dioxide.

The reaction mixture generally still contains phosphorus oxychloride in addition to the desired intermediate product, because an excess of phosphorus oxychloride is preferably used in step a). The excess phosphorus oxychloride is distilled off (step c)) over a column by lowering the pressure to 250 to 10 mbar and slowly heating the bottom to 40 to 120° C., preferably 40 to 80° C.

The methyl dichlorophosphate remaining in the bottom may likewise be distilled for the purpose of further purification. It may, however, also be reacted with the relevant long-chain alcohol without intermediate distillation.

The methyl dichlorophosphate is then reacted (step d)) with from 2 to 6 moles of a linear or branched alcohol of chain length $C_4$ to $C_{22}$. From 3 to 5 moles 2-ethylhexanol, 1-octanol, 2,2,4-trimethyl-1-pentanol, isononanol (isomer mixture), 3,5,5-trimethyl-1-hexanol, 2,6-dimethyl-4-heptanol, 1-decanol, isodecanol (isomer mixture), 1-dodecanol, 1-hexadecanol, isohexadecanol (isomer mixture), 1-octadecanol, isooctadecanol (isomer mixture), 1-eicosanol are preferably used. The alcohol may be added to the phosphorus compound, however the procedure may also be reversed and the alcohol be taken and the phosphorus compound added to it. During the addition, the heat which is liberated is removed by cooling. The temperature during the addition is preferably from 10 to 40° C., preferably 20 to 30° C.

The methyl dichlorophosphate reacts first with the alcohol to form a mixed trialkylphosphate (step d)):

$$CH_3OPOCl_2+2ROH \rightarrow CH_3OPO(OR)_2+2HCl.$$

Simultaneously and during a subsequent post-reaction the trialkylphosphate formed is cleaved by the hydrogen chloride which arises as a by-product and is dissolved in the reaction mixture, to form chloromethane and the desired dialkylphosphate (step e)):

$$CH_3OPO(OR)_2+HCl \rightarrow CH_3Cl+HOPO(OR)_2.$$

The latter reaction is carried out preferably at a temperature of from 20 to 100° C., particularly preferably 40 to 80° C.

The resulting chloromethane is less readily soluble in the reaction mixture than hydrogen chloride. Because of its low boiling point (−24° C. at standard pressure) it evaporates out of the reaction mixture and can be condensed by cooling or compressing the reaction gases. It may, however, be removed from the reaction mixture by passing through the reaction mixture inert gases such as $CO_2$, $N_2$ or air.

In order to maintain a constant HCl concentration in the reaction mixture, hydrogen chloride gas may also be admixed to the inert gas. Finally, pure hydrogen chloride may also be passed through the reaction mixture. The cleavage of trialkylphosphate is accelerated substantially by supplying hydrogen chloride and removing chloromethane.

In the final process step f), residual hydrogen chloride and any excess alcohol which is present must be removed from the reaction mixture. This may take place by washing with water, phase separation and initial distillation of the organic phase under vacuum or washing with water, driving off the excess alcohol by means of steam distillation and initial distillation of the residue under vacuum or passing through an inert gas, distilling off the alcohol by means of steam distillation and initial distillation of the residue under vacuum or passing through an inert gas and initial distillation of the reaction mixture under vacuum.

The alcohol which was used in excess is recovered in the distillate. It may be recycled into step d) of the process.

The quantity and the boiling point of the alcohol used dictate which of the working-up variants are the most favourable in step f).

The initial distillation of the reaction mixture takes place preferably at the lowest possible pressure, for example at 5 to 20 mbar, and at a bottom temperature of up to 100 to 120° C.

The residue contains the desired dialkylphosphoric acid at approx. 90% purity. The purity obtained is consequently 15 to 20 per cent higher than when phosphorus oxychloride is simply reacted with 2 moles of the desired alcohol.

The high purity of the product is surprising, since such selective cleavage of the dialkylmethyl ester of phosphoric acid, formed as an intermediate product, at the one methyl group and not at one of the two longer-chain alkyl groups could not be predicted. As a result, the methyl group functions as a readily-cleavable protective group, which temporarily blocks a P-Cl unit in the phosphorus oxychloride and consequently prevents the occurrence of the undesirable long-chain trialkylphosphate.

The chloromethane arising as a by-product represents a valuable raw material for the Rochow chlorosilane synthesis.

The invention is explained with the aid of the Example which follows:

EXAMPLE

Step a)

1.5 moles $POCl_3$ (230.25 g) are introduced into a 0.5 liter three-necked flask with an attached stirrer, thermometer and nitrogen supply line and a Claisen stillhead with an attached dropping cylinder and a gas take-off, and are cooled to 5° C. At this temperature 1 mole methanol (32 g or 40.5 ml) is added dropwise within 10 minutes, with stirring. The temperature is then maintained at 10° C. for 1 hour.

Step b)

The batch is degassed to a pressure of 50 mbar at a maximum temperature of 25° C. by the application of a water-jet vacuum.

Step c)

The excess $POCl_3$ is then distilled off over a column and a reflux divider at a pressure of 250 mbar and a bottom temperature increasing up to 112° C. There remain 136 g of bottom product, corresponding to a yield of 91% of theoretical. The quantity of distillate, at 75 g, virtually corresponds to the theoretical quantity of excess phosphorus oxychloride (76.7 g). The boiling range of the distillate is around 65–87° C.

Step d)

4 moles 2-ethylhexanol (520 g or 630 ml) are introduced into a 2-liter three-necked flask with a gas take-off and a cooling trap, and the bottom product from step c) is added to it at 10° C. within 20 minutes, with stirring.

Step e)

Stirring is continued for 4 hours at 40° C., then for 21 hours at 50° C. A quantity of 29.4 g chloromethane condenses in an attached cooling trap, corresponding to 64% of theoretical, in relation to step c).

Step f)

The product from step e) is then added to 1000 ml water in a 2-liter stirred apparatus at approx. 50° C. The organic phase is separated and undergoes initial distillation up to a temperature of 160° C. at 50 mbar. Here, 266.3 g 2-ethylhexanol distill over, corresponding to 94% of theoretical, in relation to step c). The remainder of the 2-ethylhexanol is then driven off by means of steam distillation. The residue is dried under vacuum at approx. 30 mbar and up to a maximum of 110° C., and is weighed and analysed.

278 g of residue are obtained, corresponding to 94.6% of the theoretically expected quantity of phosphoric acid di(2-ethylhexyl)ester, in relation to step c). Potentiometric titration determines the phosphoric acid di(2-ethylhexyl)ester content of the product at 89.7% and the phosphoric acid mono(2-ethylhexyl)ester content at 3.9%.

It will be understood that the specification and examples are illustrative but not limitative of the present invention and that other embodiments within the spirit and scope of the invention will suggest themselves to those skilled in the art.

What is claimed is:

1. A process for preparing a symmetrically substituted phosphoric acid diester from a long-chain linear or branched alcohol having a chain length of from $C_4$ to $C_{22}$ and phosphorus oxychloride, the process comprising the steps of:

a) reacting from 1 to 4 moles of the phosphorus oxychloride with 1 mole of methanol to form a reaction mixture comprising methyl dichlorophosphate, hydrogen chloride, and, optionally, excess phosphorus oxychloride, b) removing the hydrogen chloride from the reaction mixture, c) optionally, removing the excess phosphorus oxychloride from the reaction mixture, and optionally, purifying the methyl dichlorophosphate in the reaction mixture, d) reacting the methyl dichlorophosphate in the reaction mixture with from 2 to 6 moles of the linear or branched alcohol having a chain length of from $C_4$ to $C_{22}$ to form a product mixture comprising the symmetrically substituted phosphoric acid diester, chloromethane, and a water-soluble volatile substance, e) removing the chloromethane from the product mixture, f) removing the water soluble volatile substance from the product mixture.

2. The process according to claim 1, wherein step (a) is carried out at a temperature of from −5 to +30° C.

3. The process according to claim 1, wherein step a) is carried out by providing the phosphorus oxychloride at a temperature of from −5 to +30° C. and adding thereto the methanol with cooling.

4. The process according to claim 1, wherein from 1.3 to 2.5 moles of the phosphorus oxychloride is used in step (a).

5. The process according to claim 1, wherein the hydrogen chloride is removed from the reaction mixture in step (b) by applying a vacuum to the reaction mixture or passing an inert gas through the reaction mixture.

6. The process according to claim 5, wherein the inert gas of step (b) is air, nitrogen, or carbon dioxide.

7. The process according to claim 1, wherein the excess phosphorus oxychloride is removed from the reaction mixture in step (c) by distilling it off.

8. The process according to claim 7, wherein the methyl dichlorophosphate is purified in the reaction mixture in step (c) by distilling off impurities.

9. The process according to claim 1, wherein the linear or branched alcohol of step (d) is 2-ethylhexanol, 1-octanol, 2,2,4-trimethyl-1-pentanol, isononanol (isomer mixture), 3,5,5-trimethyl-1-hexanol, 2,6-dimethyl-4-heptanol, 1-decanol, isodecanol (isomer mixture), 1-dodecanol, 1-hexadecanol, isohexadecanol (isomer mixture), 1-octadecanol, isooctadecanol (isomer mixture), and 1-eicosanol.

10. The process according to claim 9, wherein the branched alcohol of step (d) is 2-ethylhexanol.

11. The process according to claim 1, wherein the methyl dichlorophosphate and the linear or branched alcohol are added together in step (d) at a temperature of from 10 to 40° C. and the subsequent reactions are carried out at a temperature of from 20 to 100° C.

12. The process according to claim 1, wherein the chloromethane is removed from the product mixture in step (e) by evaporating the chloromethane out of the product mixture and condensing it, or passing a gas through the product mixture.

13. The process according to claim 12, wherein the gas in step (e) is hydrogen chloride gas, an inert gas, or a mixture thereof.

14. The process according to claim 13, wherein the inert gas of step (e) is air, nitrogen, or carbon dioxide.

15. The process according to claim 1, wherein the water-soluble volatile substance of step (d) is hydrogen chloride, alcohol, or a mixture thereof.

16. The process according to claim 1, wherein the water-soluble volatile substance is removed in step (f) by:
   i) washing the product mixture with water,
   ii) phase separating organic and inorganic phases from the product mixture, and
   iii) distilling the organic phase under a vacuum.

17. The process according to claim 1, wherein the water-soluble volatile substance is removed in step (f) by:
   i) washing the product mixture with water,
   ii) steam distilling off excess alcohol from the product mixture to form a residue, and
   iii) distilling off volatile impurities under a vacuum.

18. The process according to claim 1, wherein the water-soluble volatile substance is removed in step (f) by:
   i) passing an inert gas through the product mixture,
   ii) steam distilling off excess alcohol from the product mixture to form a residue, and
   iii) distilling off volatile impurities under vacuum.

19. The process according to claim 1, wherein the water-soluble volatile substance is removed in step (f) by:
   i) passing an inert gas through the reaction mixture, and
   ii) distilling off volatile impurities under vacuum.

* * * * *